United States Patent [19]

Bhat et al.

[11] Patent Number: 5,811,613
[45] Date of Patent: Sep. 22, 1998

[54] PROCESS FOR THE PRODUCTION OF PARA-DIETHYLBENZENE

[75] Inventors: Yajnavalkya Subray Bhat; Jagannath Das; Anand Bhimrao Halgeri, all of Gujarat, India

[73] Assignee: Indian Petrochemicals Corporation Limited, Gujarat, India

[21] Appl. No.: 628,504

[22] Filed: Apr. 5, 1996

[51] Int. Cl.⁶ ........................................... C07C 2/66
[52] U.S. Cl. ............................. 585/467; 585/446
[58] Field of Search ..................... 585/446, 454, 585/467, 469

[56] References Cited

U.S. PATENT DOCUMENTS

| | | | |
|---|---|---|---|
| 4,117,026 | 9/1978 | Haag et al. | 260/671 R |
| 4,386,230 | 5/1983 | Hogan et al. | 585/467 |
| 4,677,240 | 6/1987 | Carlson et al. | 585/488 |
| 4,973,781 | 11/1990 | Valyocsik et al. | 585/467 |

*Primary Examiner*—Glenn Caldarola
*Assistant Examiner*—Thuan D. Dang
*Attorney, Agent, or Firm*—Ladas & Parry

[57] ABSTRACT

A selective, simple and efficient process for single step alkylation of ethylbenzene with ethanol, in the presence of catalytically effective amount of pore size controlled and preconditioned gallo aluminosilicate zeolite is disclosed. The process comprises subjecting a feed mixture of ethylbenzene, ethanol and optionally one or more of the reaction product/byproduct in contact with the catalyst under a chosen set of conditions. The product para-diethylbenzene can be recovered directly from the reactor effluent, by simple distillation, avoiding complicated separation processes, with a high purity sufficient for commercial application.

13 Claims, 1 Drawing Sheet

PROCESS FOR THE PRODUCTION OF PARA-DIETHYLBENZENE

BACKGROUND OF THE INVENTION

1. Field of the Invention

The present invention relates to a highly selective process for the catalytic ethylation of ethylbenzene to produce para-ethylbenzene. More particularly, the invention relates to an alkylation process for the production of para-diethylbenzene wherein a mixture of ethylbenzene and ethanol is reacted at atmospheric pressure over an improved high silica pore size regulated zeolite catalyst. This catalyst which exhibits unique shape selective effect during alkylation comprises a variable mixture of alumina, silica and pore size regulated crystalline galloaluminosilicates.

2. Description of Prior Art

Diethylbenzene has three isomers, namely ortho-, para- and meta. The para isomer is industrially more important than that of the two other isomers. It is a high value chemical having immense industrial importance by virtue of its utility as a desorbent in the selective separation of para-xylene from isomeric $C_8$ raffinate by the well known "Parex" process innovated by UOP. The demand for para-diethylbenzene (PDEB) is bound to increase in the coming years. Hence the process for the manufacture of PDEB has immense techno-economical significance.

Diethylbenzene can conveniently be synthesized by using the existing alkylation catalyst like $AlCl_3$—HCl, HF, $BF_3$ and the unmodified ZSM-5. However, the conventional catalyst is not highly selective to the para isomer. Therefore the isomers of the aforesaid ortho-, meta- and para- diethylbenzene can result according to the ratio of thermodynamics. The thermodynamic equilibrium composition of the three isomers at 700 K are as follows: ortho-diethylbenzene:meta-diethylbenzene:para-diethylbenzene= 19:54:27

These isomers have very close boiling point to each other, the relative volatility is nearly 1. Hence the separation is difficult and the cost of operation is quite expensive. With $AlCl_3$—HCl catalyst, not only the separation is difficult, but it is impossible to avoid the loss of raw material due to multiple alkylation. Moreover the catalyst is liable to cause serious pollution and corrosion problems due to its strong acidity.

A new type of zeolite catalyst, which is known as ZSM-5, was developed by Mobil Oil Corporation in 1972 has been used for alkylation reactions. The particulars of the method of production of ZSM-5 catalyst were disclosed in U.S. Pat. No. 3,702,886 and the details of the alkylation of revealed in the article published in the Oil and gas Journal, Sep. 26, 1977 by P. J. Lewis. The pores of this sort of catalyst have a uniform pore size, therefore, hydrocarbons smaller than pore dimension are adsorbed and larger hydrocarbons are repelled. Hence it is frequently referred to as a "molecular sieve". There are many precedents in the industry making use of this characteristics to conduct chemical reactions. The ZSM-5 catalyst is characterized by its selectivity, being able to satisfy the needs for high selectivity to products of different molecules, but its selectivity still falls short of expectation in resect of isomers of same kind of product. For instance, when toluene was alkylated with methanol over ZSM-5 catalyst, selectivity is very high for xylenes, but the ratio of isomers of xylenes namely ortho-, meta-, and para-xylene remains near the thermodynamic equilibrium composition. The details are reported in J. of Catalysis. vol 67, page 159, 1981 by W. W. Kaeding, C. Chu, L. B. Young, B. Weinstein and S. A. Butter.

Various techniques to enhance the shape selectivity of medium pore aluminosilicates, have been reported. These modifications enable one to obtain very high product selectivity among dialkylbenzenes during monoalkylbenzene alkylation. In the conventional modification method, the zeolite is impregnated with magnesium, phosphorous and boron oxides which result in high para selectivity. However there are several disadvantages of this modified catalyst for instance (i) the degree of modification is difficult to control and (ii) the selectivity and activity would change after regeneration. These have been overcome by Niwa and co-workers who have developed a new technique, the chemical vapor deposition of tetraethyl orthosilicate to control the pore opening size of ZSM-5. The enhancement of the para product selectivity was remarkable in xylenes formed by toluene methylation. The silicon modified ZSM-5 catalyst, its preparation and use for synthesizing high purity para-diethyl benzene from monoalkylbenzene have been reported by Ikai Wang and co-workers in U.S. Pat. No. 4,950,835 (1990). There is no doubt, therefore, that the catalysts employed for the alkylation of ethylbenzene with ethanol or ethylene thereby have met with a fairly high degree of success from the point of obtaining 97–98% para-diethylbenzene selectivity. Nevertheless, there is still room for improvement both from the process angle as well as from the point of view of the catalyst employed.

Accordingly, it is an object of this invention to provide a process for the alkylation of ethylbenzene employing a highly selective catalyst which permits the process to be operated with a very high selectivity for para-diethylbenzene with little loss of the reactants in side reactions.

A further object of the invention lies in the process for alkylation of ethylbenzene with ethanol which operates with alcohol concentration in the range 10–99%, hence best suited for a country like India, which has bio-ethanol in abundance.

Another object lies in a process for ethylation of ethylbenzene wherein the catalyst employed maintains its activity and selectivity for prolonged periods.

Yet another object lies in a process for ethylation of ethylbenzene wherein the catalyst at the end prolonged period of use, may be regenerated to get back the original activity.

In recent years, the art of catalyst making has undergone a rapid change and it has witnessed the development of a catalyst for single step catalytic alkylation of ethylbenzene and ethanol which is the subject of an Indian Patent Application No 261/BOM/1992 filed by Bhat and co-authors. This present catalyst represents a considerable improvement over the catalyst hitherto known.

The present invention has further improved over the above mentioned catalyst through the provision of a high silica zeolite catalyst comprising a mixture of amorphous silica and crystalline galloaluminosilicate preferably provided on an alumina support. In an alternative form, the catalyst components can be mixed with water to form an extrudable mass which is then extruded and the extrudates then dried and calcined, for instance at 813° K for 8 hours. By employing the improved catalyst, it is possible according to the present invention to alkylate ethylbenzene with ethanol selectively to para-diethylbenzene in a single step.

SUMMARY OF THE INVENTION

Accordingly, the present invention provides a process for the manufacture of para-diethylbenzene by catalytic alkylation of ethylbenzene which comprises subjecting a mixture of ethylbenzene and ethanol to a temperature of from 523° to 723° K in the presence of an improved catalyst comprising a pore size regulated high silica galloaluminosilicate zeolite composite in acid form whereby the ethylation takes place selectively and diethylbenzenes formed contain 95–100% para isomer, cooling the reaction medium, separating by any known means, top product consisting of unreacted ethylbenzene, withdrawing the heavier bottom product rich in para-diethylbenzene to separate therefrom para-diethylbenzene in any known manner.

DESCRIPTION OF THE PREFERRED EMBODIMENTS

Figure 1:
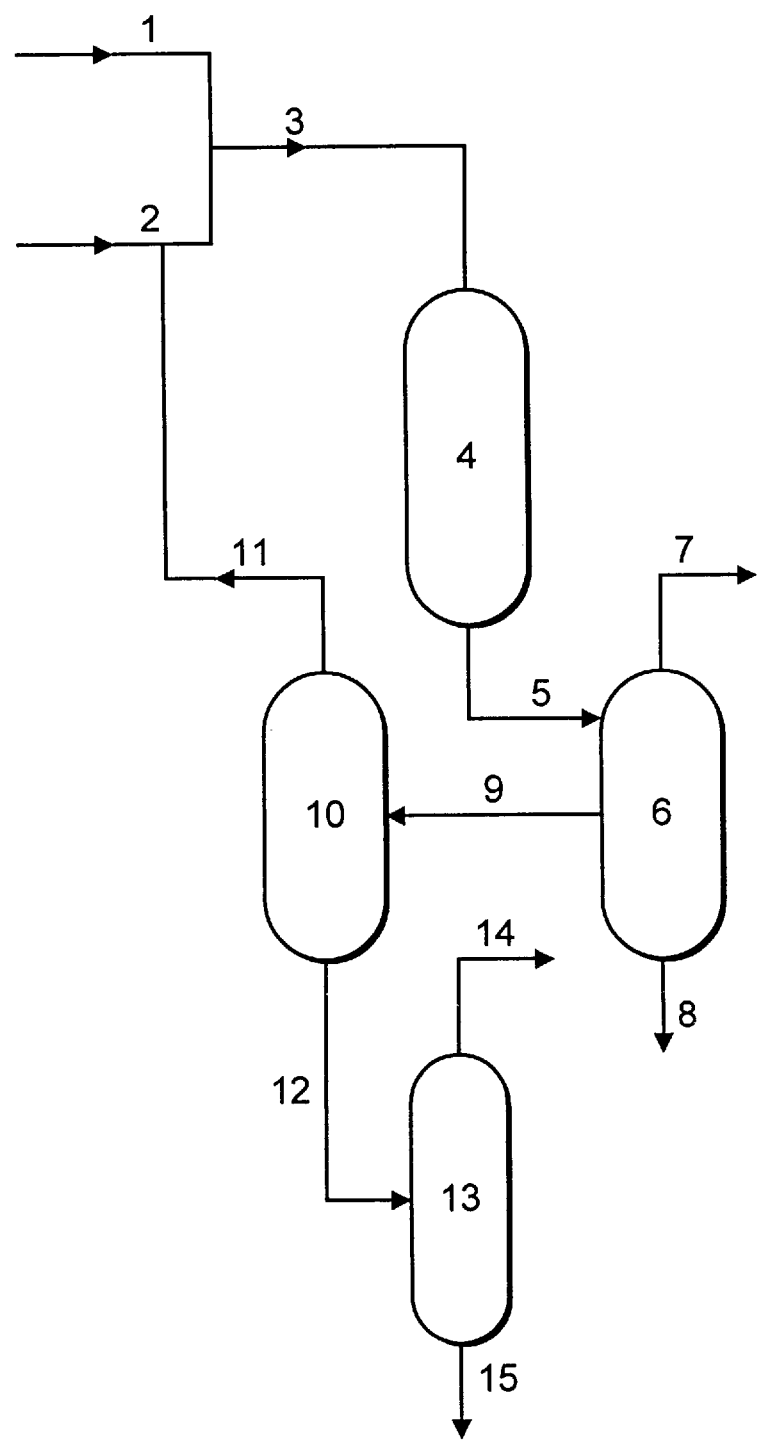
FIG. 1 is a flow diagram of the process for the production of para-diethylbenzene.

According to a preferred embodiment, the high silica zeolite catalyst comprises a mixture of amorphous silica and pores size regulated galloaluminosilicate on an alumina support. The silica to alumina molar ratio of from 70 to 500 and the silica to gallium molar ratio of from 1000 to 1500 are recommended. The pore size regulation is done with a silica precursor compound preferably tetraethyl orthosilicate. The initial activity and selectivity of the catalyst was adjusted by pretreating the catalyst with one of the reactants. The reaction is preferably effected in the absence of any carrier gas.

Reaction temperature can vary but is preferably in the range of from 523° to 723° K. The reaction is carried out at a weight hourly space velocity (WHSV) of from 0.5 to 10 $h^{-1}$ and the mole ratio of ethylbenzene to ethanol can be in the range of from 25:1 to 2:1. The aqueous alcohol employed in the reaction can have concentration from 10–99%.

In accordance with a further feature of the invention, the product stream remaining after separation which is rich in ethylbenzene is recycled to the start of the reaction. The recycled ethylbenzene stream can contain from 0.5 to 10% benzene.

One particular embodiment of the invention is now described with reference to the accompanying drawing which illustrates a flow-diagram representative of the commercial process of the invention. With reference to such drawing ethanol is supplied through line 1 while ethylbenzene through line 2, the mixture of these are heated to the reaction temperature and supplied through line 3 to the reactor. The essential reaction that takes place in the reactor 4 is the selective ethylation of ethylbenzene. However, simultaneously secondary reactions also take place over the catalyst. These include dealkylation of ethylbenzene, and dehydration of ethanol to ethylene, indeed reaction conditions can be optimized to produce a desired product pattern. The reaction products of reactor 4 are cooled therein and then led by line 5 to stabilizer 6. In stabilizer 6 the lighter product like ethylene which forms only in traces are separated and withdrawn from the top via line 7. The clearly separated water is removed from the bottom line 8. From the middle portion of the stabilizer the stream containing aromatic hydrocarbons are withdrawn and fed to the distillation column 10 via line 9. From the top of distillation column 10 unreacted ethylbenzene is recovered and recycled back to the reactor via line 11. The bottom of column 10 is sent via line 12 to another distillation column 13 to purify para-diethylbenzene. In this distillation column 13, para-diethylbenzene is recovered from the top and withdrawn via line 14, while heavier alkylaromatics are discharged via line 15.

Essentially, the improved catalyst employed in the process of present invention fulfills the optimum requirement of such a catalyst namely, it is active to selectively alkylate ethylbenzene in the para position but inactive for cracking the alkyl group of ethylbenzene and para-diethylbenzene to other undesired alkylaromatics. Where a selective alkylation process is involved, the activity of the catalyst is expressed in terms of conversion of ethylbenzene and selectivity in terms of fraction of para-diethylbenzene among diethylbenzenes formed. These terms are calculated according to the following equations:

$$EB \text{ conversion}(wt\ \%) = \frac{(wt\ \%\ EB\ \text{in feed} - wt\ \%\ EB\ \text{in product})}{wt\ \%\ EB\ \text{in feed}} \times 100$$

$$PDEB \text{ selectivity}(wt\ \%) = \frac{wt\ \%\ PDEB\ \text{in product}}{wt\ \%\ DEB\ \text{in product}} \times 100$$

The present invention now will be described at length and in greater detail in the following non-limitative examples. In particular, the examples underline the fact that the reaction conditions under which the invention can be conducted can vary depending on the content of the feed and on the composition desired in the final product mixture.

EXAMPLE 1

A series of four test runs were conducted in a commercial reactor under simulated conditions which varied the reaction temperature of each run but maintained the other parameters constant as follows WHSV=2 $h^{-1}$
EB:Ethanol mole ratio=12:1

Before the start of the run, the catalyst was initially pretreated with ethylbenzene. The results are presented in the table below

TABLE 1

| Effect of reaction temperature on the catalyst performance | | | | |
|---|---|---|---|---|
| | Run 1 | Run 2 | Run 3 | Run 4 |
| Temperature K. | 553 | 573 | 593 | 613 |
| EB Conversion, % | 4.5 | 6.5 | 7.0 | 8.0 |
| DEB Selectivity, % | 86 | 84 | 80 | 76 |
| PDEB Selectivity, % | 97.5 | 98.0 | 98.0 | 98.0 |

The results given above indicate that the reaction temperature plays a crucial role in deciding EB conversion with desired PDEB selectivity.

EXAMPLE 2

As in example 1 a series of test runs were conducted under simulated conditions but in this instance, WHSV varied in each run, the other reaction conditions being maintained constant as follows Temperature=593 K
EB:Ethanol=12:1

Like in example 1, the catalyst was initially pretreated with ethyl benzene and the results are summarized in Table 2.

TABLE 2

Effect of WHSV variation on ethylbenzene conversion

|  | Run 1 | Run 2 | Run 3 |
|---|---|---|---|
| WHSV, $h^{-1}$ | 1.0 | 2.0 | 3.0 |
| EB Conversion, % | 9.0 | 7.0 | 4.0 |
| DEB Selectivity, % | 70 | 80 | 88 |
| PDEB Selectivity, % | 96.5 | 98.0 | 98.5 |

When WHSV was varied from 1 to 4 $h^{-1}$ benzene formation and EB conversion decreased.

EXAMPLE 3

A series of three test run were conducted like in example 2 but in this instance, mol ratio of EB:Ethanol was varied in respect of each run, the other parameters being maintained constant as follows.

Temperature=603 K
WHSV=2.0 $h^{-1}$

TABLE 3

Effect of mol ratio of EB:Ethanol variation on catalyst performance

|  | Run 1 | Run 2 | Run 3 |
|---|---|---|---|
| EB:Ethanol, mol ratio | 12:1 | 10:1 | 8:1 |
| EB Conversion, % | 7.5 | 8.5 | 9.8 |
| DEB Selectivity, % | 78 | 80 | 82 |
| PDEB Selectivity, % | 98.0 | 98.4 | 98.6 |

Lower mol ratio of EB:Ethanol enhances EB conversion as well as PDEB selectivity.

EXAMPLE 4

As in example 2, a series of three test runs were conducted under simulated conditions but in this instance, it was water content in the alcohol was varied in respect of each run, the other parameters being constant as follows Temperature=593 K
WHSV=2 $h^{-1}$
EB:Ethanol=12:1

TABLE 4

|  | Run 1 | Run 2 | Run 3 |
|---|---|---|---|
| Water content in alcohol, % | 1 | 7 | 15 |
| EB Conversion, % | 7.2 | 6.5 | 5.7 |
| DEB Selectivity, % | 78 | 77 | 76 |
| PDEB Selectivity, % | 98.0 | 98.0 | 98.0 |

Higher water content decreases EB conversion and water plays the role of a diluent.

EXAMPLE 5

As in example 2, a series of three test runs were conducted under simulated conditions, but in this instance, it was the benzene content in ethylbenzene which was varied in respect of each run, the other parameter being maintained constant as follows.

Temperature=593 K
WHSV=1 $h^{-1}$
Aromatics:Alcohol mol ratio=12:1

The catalyst was pretreated with ethylbenzene before start of each run, and the performance of the catalyst in these runs are depicted in Table 5.

TABLE 5

|  | Run 1 | Run 2 | Run 3 |
|---|---|---|---|
| Benzene content in EB, wt % | 0 | 2 | 5 |
| EB Conversion, % | 7.2 | 6.5 | 5.5 |
| DEB Selectivity, % | 79 | 95 | 99 |
| PDEB Selectivity, % | 98.0 | 98.0 | 98.0 |

Presence of benzene in EB feed enhances the DEB selectivity.

EXAMPLE 6

In order to assess the stability of the improved zeolite catalyst employed in the invention a test run was carried out for 60 days in which WHSV was maintained 2 $h^{-1}$, EB:Ethanol mol ratio was kept 10:1 and initial temperature during the start of the run was 573 K and temperature increment was given to maintain iso-conversion of ethylbenzene, 5 to 6% throughout. The details are depicted in Table 6 given below.

TABLE 6

Time on stream behaviour of the catalyst

|  | Time on stream, hour | | | |
|---|---|---|---|---|
|  | 1 | 500 | 1000 | 1440 |
| Temperature K. | 573 | 578 | 603 | 618 |
| EB Conversion, % | 6.0 | 5.9 | 6.1 | 5.8 |
| DEB Selectivity, % | 98 | 97 | 98 | 98 |
| PDEB Selectivity, % | 98 | 98.5 | 98.6 | 99.0 |

As it is evident from Table 6 that the catalyst has got very good selectivity, even after 1440 hours of operation, the catalyst bed temperature reached only 618 K.

EXAMPLE 7

For a comparative assessment of the improved zeolite catalyst of the invention both when employed as a fresh catalyst and after regeneration thereof, three test runs were carried out in respect of the same catalyst. Each of these tests was effected under identical reaction conditions, viz a temperature of 593 K, a weight hourly space velocity of 2 $h^{-1}$ and a mol ratio of ethylbenzene to ethanol 12:1.

The catalyst was pretreated with EB before each run. The results of each of three tests are set out in Table 7 given below.

TABLE 7

Regenerability of the catalyst

|  | Fresh catalyst | Catalyst regenerated once | Catalyst regenerated twice |
|---|---|---|---|
| On stream, hour | 75 | 89 | 112 |
| EB Conversion, % | 6.9 | 6.8 | 6.7 |
| DEB selectivity, % | 80 | 80 | 80 |
| PDEB selectivity, % | 98 | 98 | 98 |

The data given above establish that even after successive regenerations, the catalyst of the invention does not show any appreciable loss in activity or selectivity. This is indicative of excellent stability of the catalyst. The results also suggest that the catalyst of the invention will have a longer average cycle length than earlier catalyst.

The foregoing description and the examples are provided for the purpose of guiding persons skilled in the art and it must be appreciated that the invention is not restricted only thereto. Other modifications and embodiments of the invention are clearly possible within the scope of what has been described herein.

We claim:

1. A process for the production of para-diethylbenzene by catalytic alkylation of ethylbenzene with ethanol which comprises a) subjecting a feed mixture of ethylbenzene and ethanol and a co-feed of water and benzene to a temperature ranging from 523° to 723° K in the absence of any carrier gas and in the presence of gallo alumino silicate zeolite catalyst in acid form, said catalyst comprising a mixture of amorphous silica and pore size regulated crystalline galloaluminosilicate in which the silica to alumina mole ratio is from 70 to 500 and the silica to gallium oxide mole ratio is from 1000 to 1500 provided on an alumina support wherein the catalyst is pretreated with ethylbenzene, wherein ethylbenzene is selectively ethylated to produce selectively para-diethylbenzene, and b) separating the reaction product into a lighter top product ethylbenzene and heavier bottom product para-diethylbenzene.

2. A process as claimed in claim 1, wherein the catalyst is employed in the form of an extrudate of the components thereof mixed with water to an extrudable mass, extruded, dried and calcined.

3. A process as claimed in claim 1, wherein the reaction is effected at a weight hourly space velocity (WHSV) of from 0.5 to 10 h$^{-1}$.

4. A process as claimed in claim 1, wherein ethylbenzene to ethanol mol ratio is from 40:1 to 1:1.

5. A process as claimed in 1, wherein aqueous ethanol of concentration 10 to 99% is employed in the reaction.

6. A process as claimed in claim 1 wherein tetraethyl orthosilicate is used as a modifying agent to regulate the pore size of the catalyst.

7. A process according to claim 1 wherein the ethylbenzene that is separated from the para-diethylbenzene is recycled into the process for the production of para-diethylbenzene said recycled ethylbenzene stream containing from 0 to 30% benzene.

8. A process for the production of para-diethylbenzene by catalytic alkylation of ethylbenzene with ethanol which comprises subjecting a feed mixture of ethylbenzene and ethanol, along with one or more co-feeds selected from the reaction products, the side products or both of the ethylation process to a temperature ranging from 523° to 723° K, in the absence of any carrier gas, and in the presence of galloaluminosilicate zeolite catalyst in acid form, said catalyst comprising a mixture of amorphous silica and pore size regulated crystalline galloaluminosilicate in which the silica to alumina mole ratio is from 70 to 500 and the silica to gallium oxide mole ratio is from 1000 to 1500, provided on an alumina support, wherein the catalyst is pretreated with ethylbenzene, wherein ethylbenzene is selectively ethylated to produce selectively para-diethylbenzene, separating the reaction product into a lighter top product and a heavier bottom product wherein the bottom product is para-diethylbenzene.

9. A process as claimed in claim 8 wherein tetraethyl orthosilicate is used as a modifying agent to regulate the pore size of the catalyst.

10. A process according to claim 8 wherein the ethylbenzene that is separated from the para-diethylbenzene is recycled into the process for the production of para-diethylbenzene said recycled ethylbenzene stream containing from 0 to 30% benzene.

11. A process as claimed in claim 8 wherein the catalyst is employed in the form of an extrudate of the components thereof mixed with water to an extrudable mass, extruded, dried and calcined.

12. A process as claimed in claim 8 wherein the reaction is effected at a weight hourly space velocity (WHSV) of from 0.5 to 10 h$^{-1}$.

13. A process as claimed in claim 8 wherein the ethylbenzene to ethanol mole ratio is from 40:1 to 1:1.

* * * * *